United States Patent [19]

Turner et al.

[11] Patent Number: 5,217,876
[45] Date of Patent: * Jun. 8, 1993

[54] METHOD FOR DETECTING MICROORGANISMS

[75] Inventors: James E. Turner, Chapel Hill; Thurman C. Thorpe; James L. DiGuiseppi, both of Durham; Richard C. Driscoll, Raleigh, all of N.C.; Michael J. Calandra, Somerset, N.J.

[73] Assignee: Akzo N.V., Arnhem, Netherlands

[*] Notice: The portion of the term of this patent subsequent to Jul. 31, 2007 has been disclaimed.

[21] Appl. No.: 866,130

[22] Filed: Apr. 7, 1992

Related U.S. Application Data

[63] Continuation of Ser. No. 322,874, Apr. 13, 1989, abandoned, which is a continuation-in-part of Ser. No. 168,291, Mar. 15, 1988, Pat. No. 4,945,060.

[51] Int. Cl.$^5$ ............................................. C12Q 1/04
[52] U.S. Cl. .................................... 435/34; 435/291; 435/808; 422/52
[58] Field of Search ............... 435/291, 287, 289, 808, 435/34, 39; 422/52

[56] References Cited

U.S. PATENT DOCUMENTS

| | | |
|---|---|---|
| Re. 31,879 | 5/1985 | Lubbers . |
| 2,880,070 | 3/1959 | Gilbert . |
| 3,067,015 | 12/1962 | Lawdermilt ..................... 435/304 |
| 3,313,712 | 4/1967 | George . |
| 3,676,679 | 7/1972 | Waters . |
| 3,853,712 | 12/1974 | House et al. . |
| 3,998,591 | 12/1976 | Eckfeldt . |
| 4,003,709 | 1/1977 | Eaton et al. . |
| 4,004,981 | 1/1977 | Hurni et al. . |
| 4,073,691 | 2/1978 | Ahnell et al. . |
| 4,101,383 | 7/1978 | Wyatt et al. . |
| 4,152,213 | 5/1979 | Ahnell . |
| 4,182,656 | 1/1980 | Ahnell et al. . |
| 4,201,548 | 5/1980 | Tamaoku et al. . |
| 4,236,211 | 11/1980 | Arvesen . |
| 4,285,697 | 8/1981 | Neary . |
| 4,289,248 | 9/1981 | Lynn . |
| 4,306,877 | 12/1981 | Lübbers . |
| 4,330,622 | 5/1982 | Desai . |

(List continued on next page.)

FOREIGN PATENT DOCUMENTS

| | | |
|---|---|---|
| 472420 | 2/1973 | Australia . |
| 1204606 | 5/1986 | Canada . |
| 0104463 | 4/1984 | European Pat. Off. . |
| 0117274 | 9/1984 | European Pat. Off. . |
| 0255087 | 2/1988 | European Pat. Off. . |
| 0301699 | 2/1989 | European Pat. Off. . |
| 0333253 | 9/1989 | European Pat. Off. . |
| 2326028 | 12/1973 | Fed. Rep. of Germany . |
| 2603685 | 3/1988 | France . |
| 57-207861 | 12/1982 | Japan . |
| 61-149818 | 7/1986 | Japan . |
| 8100304 | 2/1981 | World Int. Prop. O. . |

OTHER PUBLICATIONS

McFaddin, *Biochemical Tests for Identification of Medical Bacteria*, pp. 187–193 and 108–117 (1976).

"Optical Sensors for pH and Blood Gas Analysis," H. J. Marsoner et al., IFCC Workshop, Helsinki, 1985.

"Simplex Optimization of a Fiber-Optic Ammonia Sensor Based on Multiple Indicators," T. D. Rhines et al., 60 Anal. Chem. 76–81 (1988).

"Fibre-Optic Fluorescing Sensor for Ammonia," O. S. Wolfbeis et al., 185 Analytica Chemica Acta 321–327 (1986).

*Primary Examiner*—Larry Jones
*Attorney, Agent, or Firm*—William M. Blackstone

[57] ABSTRACT

An instrument and a sealable, sterilizable vessel for detecting the presence of microorganisms in a specimen, the vessel containing a liquid culture medium and a sensor means with an indicator medium therein. Changes in the indicator medium resulting from pH change or change in $CO_2$ concentration in the medium are detected from outside the vessel.

9 Claims, 4 Drawing Sheets

U.S. PATENT DOCUMENTS

| | | |
|---|---|---|
| 4,407,959 | 10/1983 | Tsuji . |
| 4,456,380 | 6/1984 | Kondo et al. . |
| 4,476,870 | 10/1984 | Peterson et al. . |
| 4,513,280 | 4/1985 | Hannon et al. . |
| 4,557,900 | 12/1985 | Heitzmann . |
| 4,568,518 | 2/1986 | Wolfbeis et al. . |
| 4,672,039 | 6/1987 | Lundblom ............... 435/291 |
| 4,698,308 | 10/1987 | Ikeda . |
| 4,780,191 | 10/1988 | Rometti et al. . |
| 4,784,947 | 11/1988 | Noeller . |
| 4,824,789 | 4/1989 | Yafuso et al. . |
| 4,833,091 | 5/1989 | Leader et al. . |
| 4,889,992 | 12/1989 | Hoberman . |
| 4,971,900 | 11/1990 | Ahnell . |
| 5,047,331 | 9/1991 | Swaine et al. . |
| 5,094,955 | 3/1992 | Calandra et al. . |
| 5,155,019 | 10/1992 | Sussman et al. . |

METHOD FOR DETECTING MICROORGANISMS

CROSS-REFERENCE TO RELATED APPLICATION

This is a continuation of application Ser. No. 07/322,874 filed Mar. 14, 1989 now abandoned, which is a continuation-in-part of Ser. No. 07/168,291 filed Mar. 15, 1988, now U.S. Pat. No. 4,945,060, issued Jul. 31, 1990.

The present invention provides a apparatus for continuously monitoring changes in pH or $CO_2$ in a specimen using a growth medium and sealed container without entering into the container after the sample is prepared and the container sealed. As further advantages, the invention prevents constituents in the specimen from affecting colorimetric determinations and also provides a means for essentially continuously monitoring the pH or the $CO_2$ concentration in the specimen.

BACKGROUND OF THE INVENTION

The presence of microbial contamination in clinical specimens is conventionally determined by culturing the specimens in the presence of nutrients and detecting microbial activity through changes in the specimen or in the atmosphere over the specimen after a period of time. For example, in U.S. Pat. No. 4,182,656 to Ahnell et al the sample is placed in a container with a culture medium comprising a carbon 13 labelled fermentable substrate. After sealing the container and subjecting the specimen to conditions conducive to biological activity, the ratio of carbon 13 to carbon 12 in the gaseous atmosphere over the specimen is determined and compared with the initial ratio. In U.S. Pat. No. 4,152,213, a method is claimed by which the presence of oxygen consuming bacteria in a specimen is determined in a sealed container by detecting a reduction in the amount of oxygen in the atmosphere over the specimen through monitoring the pressure of the gas in the container. U.S. Pat. No. 4,073,691 provides a method for determining the presence of biologically active agents, including bacteria, in a sealed container containing a culture medium by measuring changes in the character of the gaseous atmosphere over the specimen after a period of time. A method for non-invasive detection of $CO_2$ changes in the gaseous atmosphere is taught by Suppman et al, as disclosed in EPO application 83108468.6, published Apr. 4, 1984. The methods and apparatus described in these and other publications all require either a radiometric method or the invasion of the sealed container to measure changes in the gaseous atmosphere after culturing or require special materials that permit infra-red light to pass.

Other known methods for measuring microbial contamination of specimens, particularly blood cultures, include measuring minute changes in temperature, pH, turbidity, color, bioluminescence, and impedance. Generally, these methods determine microbial contamination by detecting bacterial metabolic byproducts. Microbial contamination may also be assessed by subculturing and/or staining. Of these methods, only impedance, radiometry and infra-red spectrometry provide the possibility of automated processing of clinical specimens. And except for impedance and infra-red measurements, these procedures also require entering the container in order to make a measurement on the liquid specimen or the gaseous atmosphere over the specimen. In addition to the likelihood of contamination and creating the likelihood of altering the constituency of the atmosphere over the specimen each time a determination is made, these methods do not permit taking measurements continuously or repeatedly over short time intervals for an extended period of time. This is a significant disadvantage as the rate of growth of contaminating organisms differs depending on the organism and the number of organisms in the original sample, such that it cannot be predicted when detectable changes in the atmosphere or fluid sample will be presented by a contaminated specimen. In a related problem, when contamination is determined by pH changes in the liquid sample, various metabolic products will affect the pH of the sample differently. For example, the production of ammonia will raise the pH while the production of $CO_2$ will lower it. Different growth rates of different contaminating organisms could result in a pH increase at one time and a decrease at another time, which would not be detected if the pH is measured at widely spaced intervals. Another source of error when detecting changes by pH measurement in whole blood samples, particularly when an indicator dye is the means for pH determination, is the likelihood that the dye appearance can be affected or obscured by the presence of blood cells. Colorimetric indicators can only be effectively used if errors induced by the nature of the specimen can be prevented from influencing the appearance of the dye.

SUMMARY OF THE INVENTION

The present invention relates to an apparatus and a device for detecting the presence of microorganisms in clinical specimens, such as blood or other body fluids, by culturing the specimens with a sterile growth medium in a transparent, sealed, sterile container. The presence of microorganisms is determined by detecting or measuring changes in the pH of the specimen or the production of $CO_2$ within the specimen using a disposable sensor affixed to the interior surface of the container. According to this invention, microorganisms can be detected in the presence of interfering materials, such as large concentrations of red blood cells, through non-radiometric and non-invasive means.

BRIEF DESCRIPTION OF THE DRAWINGS

The figures consist of the following.

This drawing shows the overall appearance of the functional part of the instrument, the detector assembly, with (1) the vessel, (2) sensor, (3) culture medium, the (4) light source, (5) photodetector, and the associated electronics including (6) current source, (7) current to voltage converter and (8) low pass filter.

Each detector assembly preferably consists of a photodiode in a countersunk hole and one or more LED's arrayed such that light falls on the surface to be viewed, but not directly onto the detector itself. The electronic circuits in this embodiment include amplifiers and filters to condition the signals from the detectors, multiplexers to select among the signals available, and constant current sources for the illuminators.

The entire device was placed on an agitator inside a 37° C. incubator, which provided a suitable environment for microbial growth and excluded room light from the photodetectors.

Besides testing the instrument subjectively with various colored bottles, it was tested with the pH sensitive membrane bottles. This figure shows the average voltage output of seven different detectors after equilibration of the sensor with various buffers over a pH range of 5.8 to 8.2. Detailed studies showed the system could reliably distinguish changes of 0.1 pH unit over a range of pH 6.0 to 7.5.

The instrument was used to detect microbial growth by both pH change and by $CO_2$ production. This figure shows the change in pH and in $CO_2$ resulting from growth of the bacterium, E. coli.

Essentially all organisms will release $CO_2$ in the course of their metabolism. Thus, this system can be used to detect the growth of a very wide range of microorganisms. This figure shows the detection of $CO_2$ produced during the growth of E. coli, a Gram negative bacterium; S. pyogenes, a Gram positive bacterium; P. aeruginosa, a Gram negative non-fermenting bacterium; B. fragilis, an anaerobic bacterium; and C. albicans, a yeast. The units indicate relative $CO_2$ concentration in the medium based on $CO_2$ concentration at the beginning of the assay. Because the sample containers and media are at room temperature (approximately 20° C.), and the container and sample are incubated at 37° C. during the assay, $CO_2$ is released into the space above the liquid sample and medium during the first 2 to 4 hours because of the reduced solubility of $CO_2$ in the liquid as temperature increases. Unless the containers and media are maintained at 37° C. before introduction of the sample and placement into the instrument, reliable indication of the presence of microorganisms cannot be measured until after the minimum $CO_2$ concentration is passed, typically within the first 2 to 4 hours.

DESCRIPTION OF PREFERRED EMBODIMENTS

Figure 1:
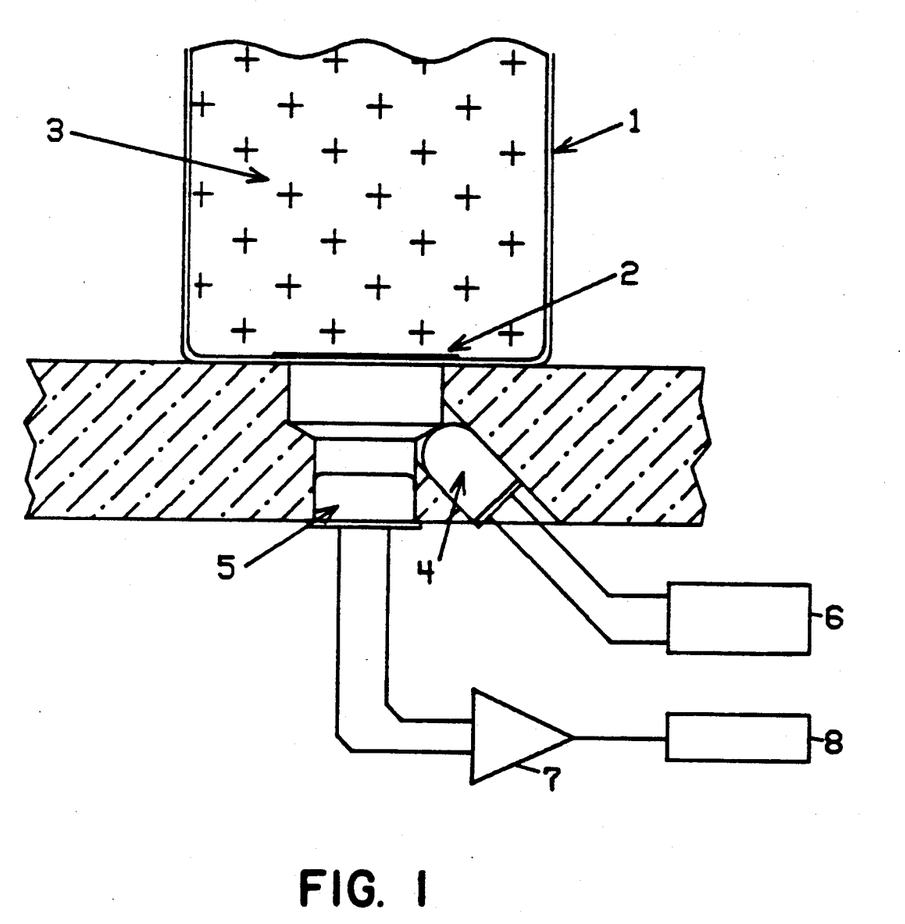
FIG. 1—Blood Culture Instrument
Figure 2:
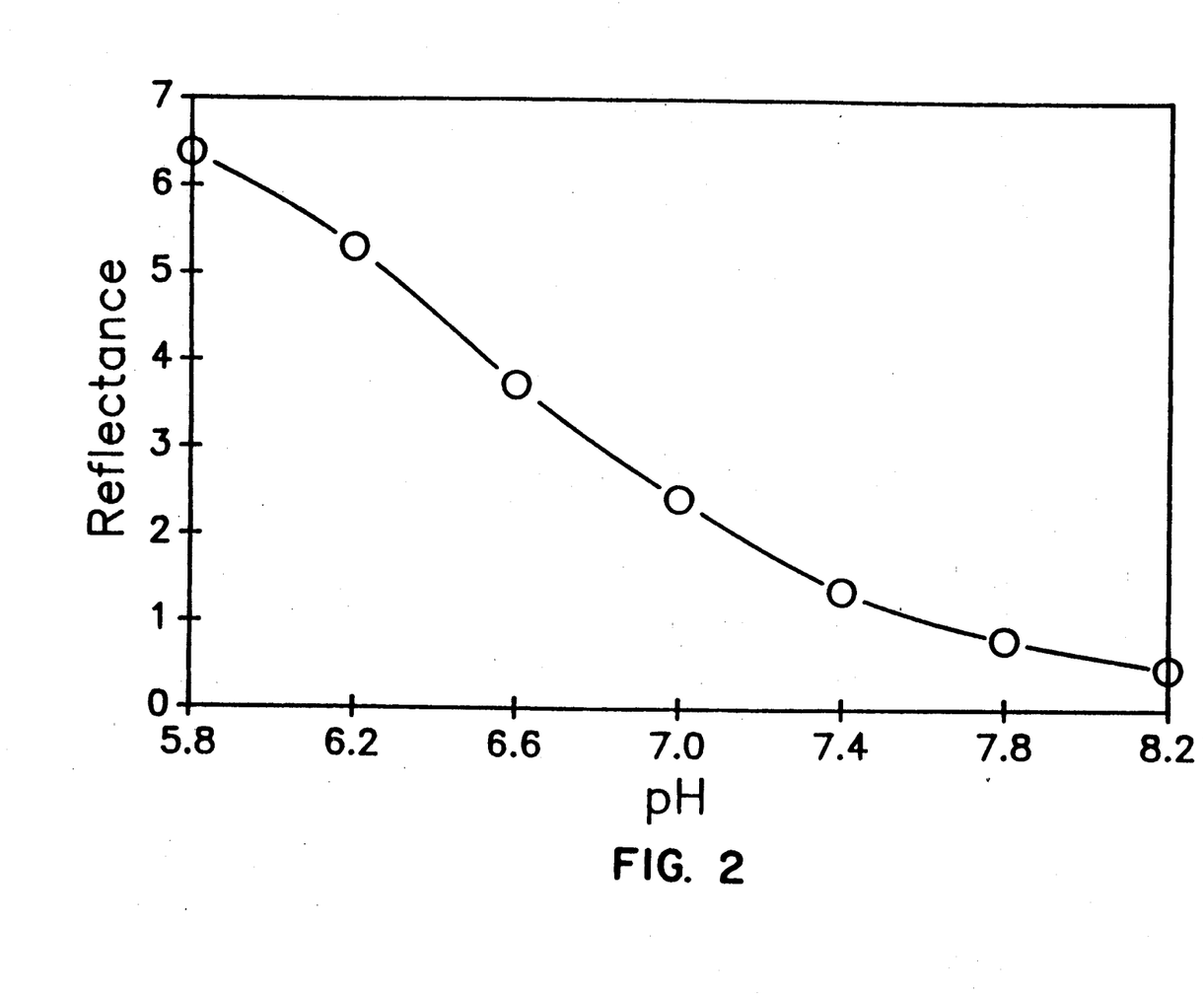
FIG. 2—pH Sensitivity
Figure 3:
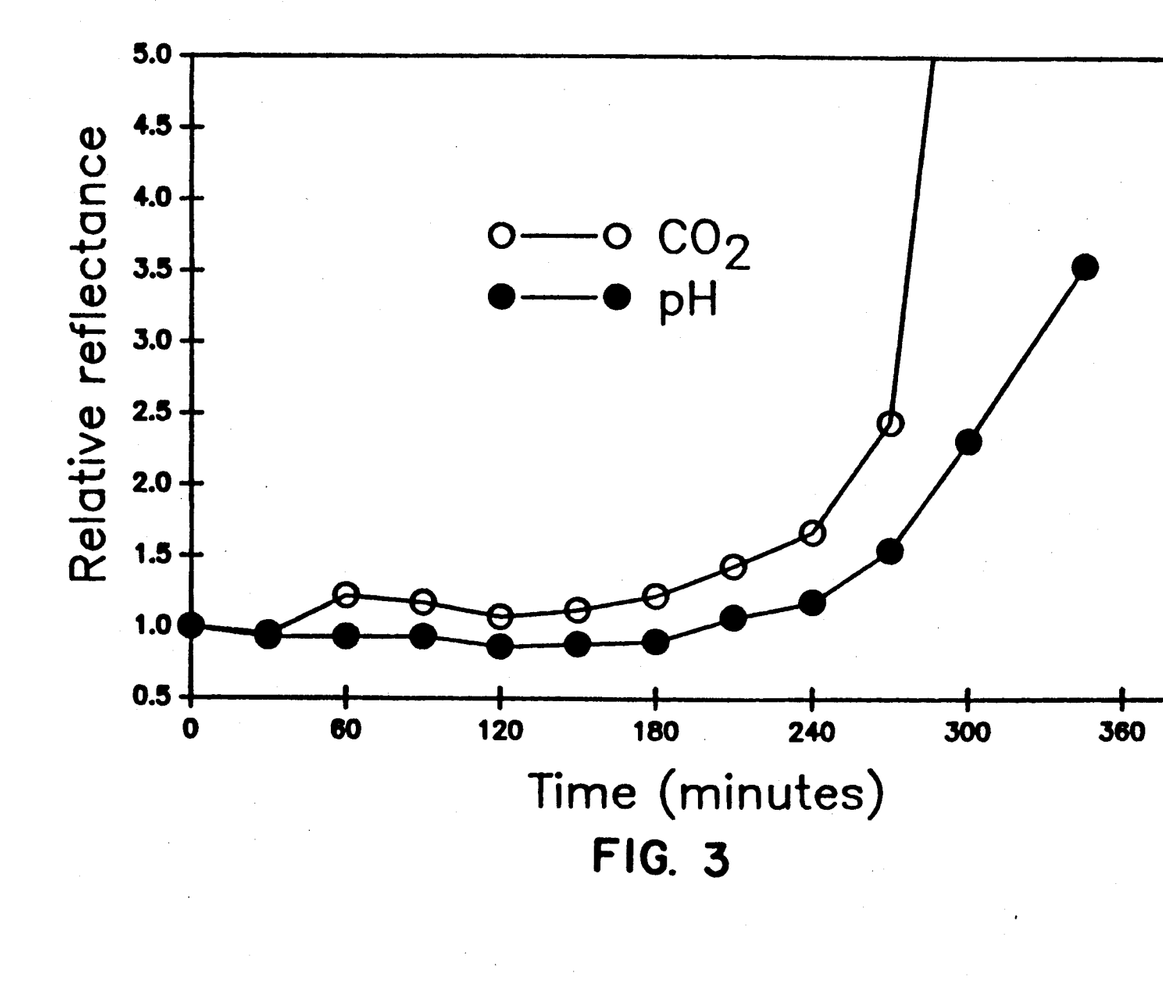
FIG. 3—pH and $CO_2$ change with microbial growth
Figure 4:
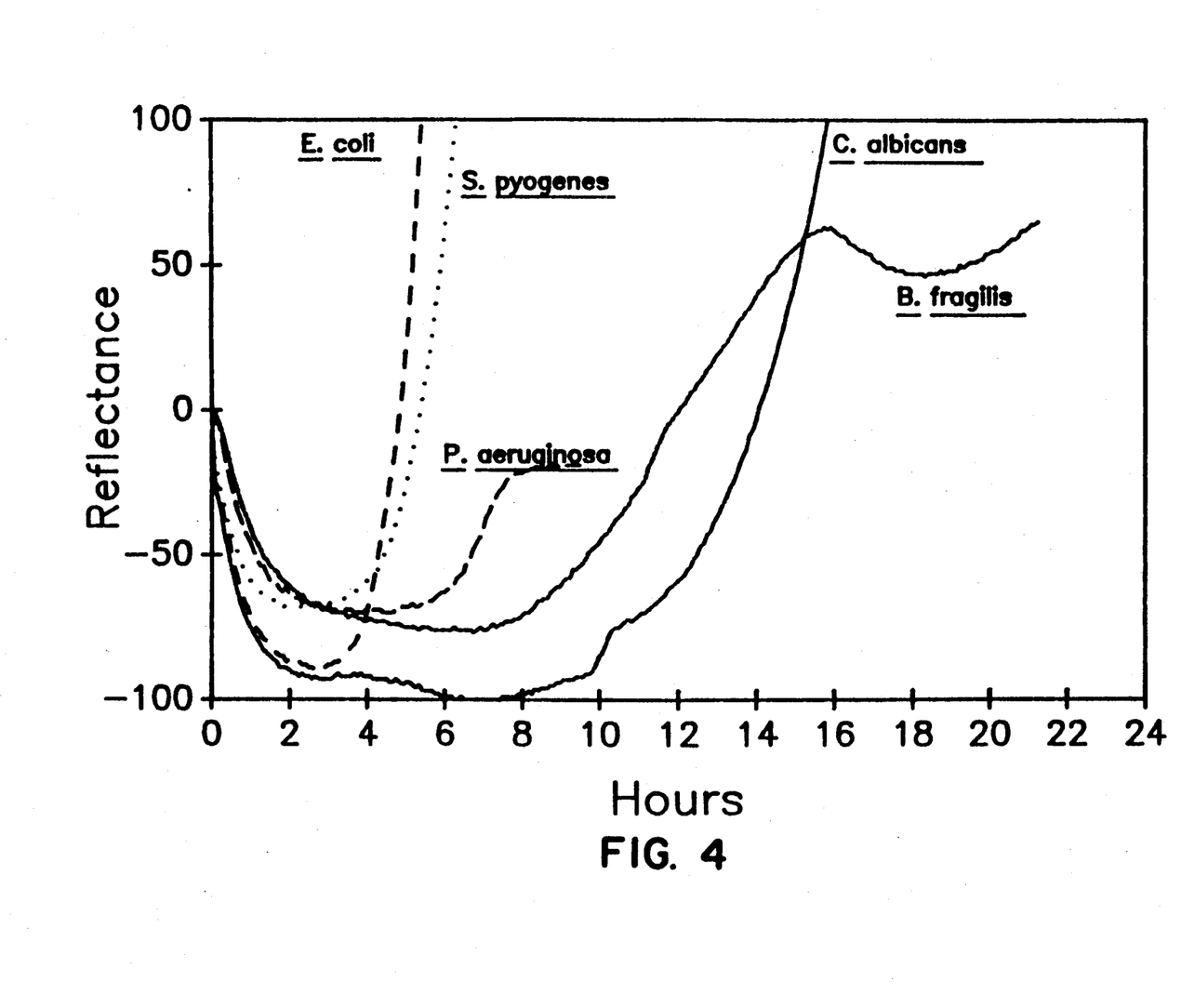
FIG. 4—Detection of a Variety of Microorganisms

The apparatus and device of the invention provide a non-invasive means for detecting the presence of microorganisms in clinical specimens, such as blood samples or other body fluids, by measuring an increase in metabolic products produced by microorganisms. The specimen is added to a specially formulated medium that enhances the production of certain microbial metabolic products, which are detected by a unique disposable sensor located at the bottom of a culture bottle. The sensor comprises a solid composition or membrane, which we refer to as an attachment or support medium, with an indicator medium immobilized on or within it. The sensor is placed flush against the inside surface of a container, such that the indicator medium is visible from outside, and sealed to prevent cells, proteins, other solids or other opaque or colored components from getting between it and the container surface. In certain embodiments the sensor is separated from the specimen and its growth medium by a membrane or solid layer that permits the passage of gas molecules but prevents passage of ions. Microorganisms in specimens of body fluids, such as blood, containing as few as 1 organism per milliliter can be detected using this invention. Such specimens may require up to 7 days incubation before the population of organisms reaches a critical level, where an increase in metabolic products can be measured. We found a concentration of $10^6$ CFU/ml for certain types of organisms provided measurable changes in pH or $CO_2$. All organisms showed measurable results at concentrations of $10^7$ to $10^8$ CFU/ml.

The invention is unique and advantageous in several respects: 1) the microbial metabolic products are measured in the liquid phase of the culture bottle rather than in the atmosphere over the specimen, 2) because the unique disposable sensor is affixed to the interior surface of the bottle, measurements can be made from outside the transparent wall of the bottle without having to violate the integrity of the bottle, 3) the external measurements can be made by visual inspection or with an instrument that measures by reflectance, 4) opaque or colored components in the specimen do not interfere with the ability of the sensor to detect changes or the measurement of those changes, and 5) a high concentration of indicator molecules is maintained within a small volume, i.e., on the membrane, such that a color change can be easily observed.

The nutritional components that make up a complex microbial medium influence the metabolic pathways used by microorganisms. Organic acids, bases and various gases are produced in proportions dependent on the nutrients available. These products also vary from species to species of microorganism. The presence of these products in the liquid medium can change it pH. The sensors used in the invention contain pH sensitive indicators that give a measurable change in response to a pH change in the environment. In the embodiment in which the pH sensor is covered by a gas-permeable, ion-impermeable membrane, the presence of gases that affect the pH of the indicator, such as $CO_2$ or ammonia, are measured. Thus, microbial growth can be detected either by changes in pH of the liquid culture medium or by measurement of gases dissolved in the medium produced by microorganisms. Carbon dioxide is a universal metabolite produced by all organisms and, therefore, is the preferred metabolite for detection of microbial growth.

$CO_2$ and pH sensors share two common components, a molecular species useful as a pH indicator and an attachment/support medium. The pH indicator can be attached either covalently or non-covalently to the support medium. Alternately, the indicator can be encapsulated within a polymer matrix that is gas permeable, such as a pH indicator emulsified within a polymer matrix prior to curing. The $CO_2$ sensor has a third component, a semi-permeable substance that completely separates the indicator membrane from the specimen and growth medium. These sensors are affixed inside a suitable transparent vessel with an appropriate adhesive.

A variety of different fluorescent and visible pH indicators can be used as the active molecular species in pH or $CO_2$ sensors. Generally, the only limitations on the selection of indicators are the requirements that they have acceptable dynamic pH ranges and wavelength changes that are readily detectable by existing front surface fluorescence or reflectance technologies.

Sensors for detecting pH changes in the culture medium according to the invention should exhibit a change in fluorescence intensity or visible color over a pH range of about 5.0 to about 8.0.

Indicators for the $CO_2$ sensor should exhibit a change in fluorescence intensity or visible color between about pH 10 and about 6 in order to detect changes in $CO_2$ concentration.

Only certain pH indicator molecules can h=bound covalently or non-covalently to a support medium and retain their pH indicating properties. We found indicators belonging to the xanthene, phenolphthalein and phenolsulfonphthalein groups to be useful. Examples of these include fluorescein, coumarin, phenolphthalein, thymolphthalein, bromothymol blue, thymol blue, xylenol blue and α-naphthol benzein.

The attachment/support medium can be a substance such as cellulose, to which a pH indicator can be covalently attached using organic reactions. Non-covalent attachment of pH indicators can be achieved using ionic support materials, such as nylon membranes that have a positive or negative zeta potential. Other ionic support materials that can be used are positive or negatively charged ionic resins, such as diethylamino ethyl (DEAE) resin or DEAE cellulose. Pretreatment of the support material with a protein may be required if the indicator membrane is to be in direct contact with the microbial growth medium.

The pH indicator sensors directly detect pH changes due to the pH environment of the microbial growth medium. However, these sensors can be made to selectively react to gases (e.g., carbon dioxide, ammonia) in the liquid growth medium by covering them with a selectively semi-permeable composition or membrane, such as silicone, latex, teflon, or various plastics characterized by the capacity to selectively permit the diffusion of a gas while preventing the passage of ions. For sensors comprising indicator encapsulated within a polymer matrix, the polymer forming the matrix can act as the semi-permeable barrier that permits the passage of gases but not ions.

In the encapsulated indicator embodiment, the $CO_2$ sensor is comprised of four components. The first component is a visual or fluorescent pH indicator, which is reactive at the pH range between 6 and 10. Examples of indicators meeting these criteria are bromothymol blue, thymol blue, xylenol blue, phenolphthalein, coumarin, and fluorescein. The second component is sodium hydroxide or an equivalent base, which maintains an optimal pH environment for detection of $CO_2$ by the selected pH indicator. The third component is glycerol or an equivalent emulsifier, which can produce micelles of indicator solution emulsified within the uncured polymer. The fourth component is the uncured polymer such as room temperature vulcanization (RTV) white silicone, which maintains a proper environment for the indicator. Any polymer can be used that does not affect the chemical activity of the indicator, either from its own chemical or physical properties or its requirements for curing, as long as it is permeable to gases but no ions, and does not have these properties altered when subjected to sterilization by autoclaving. Other silicone polymers that are also satisfactory are those that are cured by high temperature, by catalytic activity, or by ultraviolet vulcanization. An emulsion is prepared from the four components and the polymer is cured to form a semipermeable matrix around the micelles of pH indicator, which permits selective diffusion of $CO_2$ and other gases from the liquid microbial growth medium, resulting in a measurable change in the indicator. The sensor can be prepared separately, such as in a mold, cured, and then attached to the culture bottle with an appropriate adhesive, such as a silicone adhesive. Alternatively, and preferably, the sensor is formed on the bottom of the bottle and cured in situ. After curing the bottle with the sensor is sterilized, such as by autoclaving. Conveniently, the growth medium can be introduced into the bottle before autoclaving and also sterilized by that process.

The specific examples of pH and $CO_2$ sensors that follow are to provide to illustrate the invention, but not limit its scope as claimed.

EXAMPLE 1

Production of a Fluorescent pH Sensor

Cellulose dialysis tubing (Spectrapor M.W. cutoff 12,000-14,000, 0.001 inch dry thickness) was cut into 5/16 inch circles with an arch punch. The cellulose circles (1.2 grams of them) were soaked in distilled water for 30 minutes, drained, and then soaked in dry isopropanol (12 mls) for 10 minutes. The membranes were drained and placed into a 100 ml round bottom flask with a stir-bar. Dry isopropanol (50 mls) and triethylamine (5 mls) were added to the flask, and then 75 mg FITC (fluorescein isothiocyanate) were dissolved in the mixture. This mixture was refluxed with gentle stirring for five hours.

The cellulose membranes were cooled, drained, and then washed with 10 changes of 100 mls of distilled water. The saturated cellulose membranes were attached to the bottom of an appropriate glass bottle with a silicone adhesive (GE 2501 Silicone Sealant, clear). After curing, growth medium was added and the closed bottle was sterilized by autoclaving for 15 minutes at 121° C. and 15 psi.

EXAMPLE 2

Preparation of Non-fluorescent Indicator pH Sensors

Nylon membranes modified to have positive zeta potentials (Zeta Probe, BioRad) were placed in a 3% solution of Tryptic Soy Broth and soaked for one hour at room temperature with gentle shaking on a rotating shaker. Excess Tryptic Soy Broth was exhaustively washed from the nylon membranes with deionized water. The washed membranes were placed in a 0.0001 to 0.1% solution of pH indicator (bromothymol blue) dissolved in 0.1N NaOH. The membranes were allowed to react for one hour at room temperature with gentle shaking. Excess indicator solution was removed from the membranes by exhaustively washing with deionized water until no indicator appeared to be washed from the membranes. The pH indicator membranes were allowed to air dry for 24 hours and 11/16 inch circles were punched from the membranes.

The pH indicator membranes were attached to the bottom of glass vessels with a silicone adhesive (GE 2501 Silicone Sealant, clear). These bottles were filled with microbial growth medium and sterilized by autoclaving.

EXAMPLE 3

Preparation of Non-fluorescent Indicator $Co_2$ Sensors

Nylon membranes modified to have positive zeta potentials (Zeta Probe, BioRad) were placed in an indicator solution comprised of 0.001 to 0.1% xylenol blue and 0.0001 to 0.1% bromothymol blue dissolved in 0.1N NaOH. The membranes were allowed to react for one hour at room temperature with gentle shaking. After reacting with the indicator solution, the membranes were exhaustively washed with deionized water to remove excess indicator. The indicator membranes were air dried for 24 hours and 11/16 inch circles were punched from the membranes. The indicator membranes were then attached to the bottom inside surface of clear glass bottles with silicone adhesive (GE 2501 Silicone Sealant II, clear) and a second layer of the silicone adhesive was placed on top of the indicator membrane to completely seal the nylon indicator membrane.

These bottles were filled with microbial growth medium and sterilized by autoclaving.

EXAMPLE 4

Preparation of Encapsulated Indicator Sensors

Stock solutions were prepared of 0.1–1.0% phenolphthalein, xylenol blue, or bromothymol blue in 0.0005–0.5N NaOH containing 25–75% glycerol. 0.1–0.5 ml of the stock indicator-NaOH-glycerol were added to 1.0 gram of uncured RTV white silicone (GE Silicone II, white) and mixed until a fine emulsion was made. The silicone-indicator emulsion was placed into a syringe dispenser and dispensed 0.1–0.2 ml into the bottom of a glass vessel and the emulsion distributed evenly on the bottom of the glass vessel. The indicator-silicone emulsion sensor was allowed to cure for a minimum of 24 hours at ambient temperature in an atmosphere of less than 50% relative humidity. After curing, the vessels with $CO_2$ sensors were filled with microbial growth medium and sterilized by autoclaving.

Culture Medium Formulations

The medium for microbial detection by a change in pH comprises 3% Tryptic Soy Broth (DIFCO), 0.5% Proteose Peptone (DIFCO) #3, 1.25% D-glucose, and 1% L-arginine. Other components are reducing agents (0.01% L-cysteine) and an anticoagulant (0.05% SPS sodium poly-sulphonate). This medium has a low buffering capacity so that any metabolic products that affect pH will easily change the pH of the medium. Glucose is a fermentable carbohydrate that when metabolized by microorganisms results in the production of organic acids that cause a decrease in pH. Arginine is added as a substrate for those non-fermenting microorganisms (i.e. *Pseudomonas aeruginosa*) that do not normally metabolize glucose. The addition of arginine results in release of basic metabolites that cause an increase in pH of the medium. If $CO_2$ production by *Pseudomonas aeruginosa* is to be measured, arginine is not included. Other carbohydrates or amino acids can be incorporated into the medium to induce pH change when metabolized by other species of microorganisms.

Apparatus for Automatic Detection of Microbial Contamination

Both pH change and $CO_2$ production due to microbial growth may be detected and measured using the instrument described below.

The sensors monitored by this instrument contain indicators that change color when growing or metabolizing microbes are present. Although the color changes may be apparent to the naked eye, use of the instrument provides the advantages of objectivity, sensitivity, and continuity of measurement. In the preferred embodiment the instrument is essentially a visible light reflectometer that monitors the color change of the sensor. In order to allow continuous monitoring of all samples, it is preferred to have a detector for each sample. Other alternatives will be obvious to those skilled in the art, such as using conventional means to move specimen containers past one or more stationary detectors or moving one or more detectors past stationary specimens.

In the preferred embodiment solid state illuminators and detectors are used. Incandescent and arc lamp sources of illumination may also be used in conjunction with mirrors, lenses, optical fibers, and other means of directing the light to the sensor.

The various microorganisms listed in Table 1 have been detected using the invention. These results indicate that these, any other organisms of the same type, and any organisms that produce detectable gases or other products that affect the pH of the liquid medium can be detected using the invention.

TABLE 1

Enterobacteriaceae
   *Escherichia coli*
Staphylococcus spp.
   Coagulase-negative staphylococcus
   *S. aureus*
Streptococcus spp.
   *S. pneumoniae*
   Group A
   Group B
   Enterococci
Yeast
   *Candida albicans*
   *Cryptococcus neoformans*
   *Torulopsis glabrata*
Nonfermentors
   *Pseudomonas aeruginosa*
   *Acinetobacter calcoaceticus*
Anaerobes
   *Bacteroides fragilis*
   *Clostridium perfringens*
   *Fusobacterium necrophorum*
   *Peptostreptococcus anaerobius*
Other Microorganisms
   *Haemophilus influenzae*
   *Neisseria meningitidis*

We claim:

1. A method for detecting microorganisms in a specimen, comprising the steps of
    introducing the specimen under sterile conditions into a sterile specimen container, the specimen container having at least one transparent section in the wall thereof and a sensor means containing an indicator medium that exhibits a detectable change when exposed to gaseous products of an organism's metabolic activity located inside said container in the region of the transparent section,
    incubating the specimen in the specimen container with a microbial growth medium, and
    monitoring from outside the container through the transparent section thereof the production of gaseous products of an organism's metabolic activity without violating the integrity of the container by detecting changes exhibited in the indicator medium in the sensor means resulting from the gaseous products passing to the sensor means, thereby detecting the presence of microorganisms contained in the specimen.

2. The method of claim 1, wherein the changes exhibited in the indicator medium are monitored using a detector instrument.

3. The method of claim 1, wherein the specimen is in contact with the sensor means during incubation.

4. The method of claim 3, wherein the specimen and the microbial growth medium form a liquid composition, and the sensor means is submerged below the surface of that liquid composition during incubation.

5. A method for detecting microorganisms in a specimen, comprising the steps of introducing the specimen under sterile conditions into a sterile specimen container, the specimen container having at least one transparent section in the wall thereof and a sensor means containing an indicator medium that exhibits a detectable change when exposed to gaseous products of an organism's metabolic activity located inside said container in the region of the transparent section, incubating the specimen in the specimen container with a microbial growth medium, and monitoring from outside the container through the transparent section thereof the production of gaseous products of an organism's metabolic activity without violating the integrity of the container by detecting changes exhibited in the indicator medium in the sensor means resulting from the gaseous products passing to the sensor means, wherein the indicator medium in the sensor means is separated from the specimen by a semipermeable membrane, the gaseous products detected comprise $CO_2$ and the indicator medium is a molecular species responsive to pH.

6. The method of claim 5, wherein the changes exhibited in the indicator medium are monitored using a detector instrument.

7. The method of claim 5, wherein the specimen and the microbial growth medium form a liquid composition and that liquid composition is in contact with semipermeable membrane during incubation.

8. The method of claim 7, wherein the membrane is submerged below the surface of the liquid composition during incubation.

9. A method for detecting microorganisms in a specimen, comprising the steps of introducing the specimen under sterile conditions into a sterile specimen container containing a microbial growth medium, the specimen container having at least one transparent section in the wall thereof and a sensor means containing an indicator medium that exhibits a detectable change when exposed to gaseous products of an organism's metabolic activity located inside said container in the region of the transparent section, incubating the specimen in the specimen container, wherein the specimen and microbial growth medium are in contact with the sensor means during incubation, monitoring from outside the container through the transparent section thereof the production of gaseous products of an organism's metabolic activity without violating the integrity of the container by detecting changes exhibited in the indicator medium in the sensor means resulting from the gaseous products passing to the sensor means.

* * * * *